(12) United States Patent
Peng et al.

(10) Patent No.: US 7,667,071 B2
(45) Date of Patent: Feb. 23, 2010

(54) PROCESS FOR THE PREPARATION OF GABAPENTIN HYDROCHLORIDE

(75) Inventors: Zhenyun Peng, Xuzhou (CN); Wei Zhu, Xuzhou (CN)

(73) Assignee: NHWA Pharma Corporation, Xuzhou (CN)

( * ) Notice: Subject to any disclaimer, the term of this patent is extended or adjusted under 35 U.S.C. 154(b) by 72 days.

(21) Appl. No.: 11/990,681

(22) PCT Filed: Apr. 28, 2006

(86) PCT No.: PCT/CN2006/000830

§ 371 (c)(1),
(2), (4) Date: Feb. 19, 2008

(87) PCT Pub. No.: WO2007/019752

PCT Pub. Date: Feb. 22, 2007

(65) Prior Publication Data

US 2009/0099362 A1     Apr. 16, 2009

(51) Int. Cl.
*C07C 53/134* (2006.01)
*C07D 221/20* (2006.01)

(52) U.S. Cl. .................. 562/512; 546/16; 562/507

(58) Field of Classification Search .................. 546/16; 562/507, 512

See application file for complete search history.

(56) References Cited

U.S. PATENT DOCUMENTS

| 6,846,950 B2 | 1/2005 | Ferrari et al. |
| 2004/0063997 A1 | 4/2004 | Ferrari et al. |

FOREIGN PATENT DOCUMENTS

| CA | 2247237 A1 | 10/1997 |
| CN | 1109017 | 9/1995 |
| CN | 1471507 | 1/2004 |
| WO | WO-03/002517 A1 | 1/2003 |
| WO | WO-2006/000562 A1 | 1/2006 |

*Primary Examiner*—Charanjit S Aulakh
(74) *Attorney, Agent, or Firm*—Connolly Bove Lodge & Hutz LLP

(57) ABSTRACT

A process for preparation of gabapentin hydrochloride by converting 1,5-dicyano-2,4-dioxo-3-azaspiro[5,5]-undecane into 1,5-diaminoformyl-2,4-dioxo-3-azaspiro[5,5]-undecane at a temperature of 65° C. to 85° C. in the presence of a strong acid, and then carrying out Hofmann rearrangement under an alkaline condition. The starting material of the process is readily available. The process is simple, and can reduce the purification procedure of intermediates, reduce production cost, and obtain product with higher purity.

12 Claims, No Drawings

US 7,667,071 B2

PROCESS FOR THE PREPARATION OF GABAPENTIN HYDROCHLORIDE

RELATED APPLICATIONS

This application is a national stage application (under 35 U.S.C. 371) of PCT/CN2006/000830 filed Apr. 28, 2006, which claims benefit of Chinese application 200510041536.9 filed Aug. 19, 2005.

FIELD OF THE INVENTION

The present invention generally relates to a process for preparation of gabapentin hydrochloride, in particular to a process for preparation of gabapentin hydrochloride by Hofmann rearrangement. The present invention also relates to 1,5-diaminoformyl-2,4-dioxo-3-azaspiro[5,5]-undecane, which is used as an intermediate to prepare gabapentin hydrochloride, and preparation process thereof.

BACKGROUND OF THE INVENTION

Gabapentin hydrochloride is an important intermediate to synthesize gabapentin, an anti-epileptic agent, various synthesis processes for which have been reported in literatures and patents heretofore. For example, US patent application 20040034248 reports a Hofmann rearrangement process using 1,1-cyclohexanediacetic acid monoamide, and US patent application 20040063997 reports a Hofmann rearrangement process using 3,3-(pentamethylene)glutarimide.

SUMMARY OF THE INVENTION

The object of the present invention is to provide a process for preparation of gabapentin hydrochloride from readily available starting materials with simple preparation procedure, lower production cost, and higher product purity.

According to one aspect of the present invention, there is provided a process for preparation of gabapentin hydrochloride, which comprises the following steps:

(i) converting 1,5-dicyano-2,4-dioxo-3-azaspiro[5,5]-undecane into 1,5-diaminoformyl-2,4-dioxo-3-azaspiro[5,5]-undecane at a temperature of 65° C. to 85° C. in the presence of a strong acid;

(ii) subjecting the 1,5-diaminoformyl-2,4-dioxo-3-azaspiro[5,5]-undecane obtained in step (i) to Hofmann rearrangement under an alkaline condition, and then acidifying with hydrochloric acid to provide gabapentin hydrochloride.

According to another aspect of the present invention, there is further provided 1,5-diaminoformyl-2,4-dioxo-3-azaspiro [5,5]-undecane as an intermediate used in the above-mentioned process, and preparation process thereof, wherein the preparation process comprises a step of hydrolyzing 1,5-dicyano-2,4-dioxo-3-azaspiro[5,5]-undecane at a temperature of 65° C. to 85° C. in the presence of a strong acid.

DETAILED DESCRIPTION OF THE PREFERRED EMBODIMENTS

One aspect of the present invention relates to a process for preparation of gabapentin hydrochloride, which comprises:

(i) converting 1,5-dicyano-2,4-dioxo-3-azaspiro[5,5]-undecane into 1,5-diaminoformyl-2,4-dioxo-3-azaspiro[5,5]-undecane at a temperature of 65° C. to 85° C. in the presence of a strong acid;

(ii) subjecting 1,5-diaminoformyl-2,4-dioxo-3-azaspiro[5,5]-undecane obtained in step (i) to Hofmann rearrangement under an alkaline condition, and then acidifying with hydrochloric acid to provide gabapentin hydrochloride.

In the process for preparation of gabapentin hydrochloride according to the present invention, 1,5-dicyano-2,4-dioxo-3-azaspiro[5,5]-undecane used in step (i) is obtained by subjecting cyclohexanone to reacting with ethyl cyanoacetate, cyanoacetamide, and triethylamine in a lower alcohol solvent. A preferred process comprises subjecting 1 mol of cyclohexanone, 1 mol of ethyl cyanoacetate, 1 mol of cyanoacetamide, and 1 mol of triethylamine to reaction in a lower alcohol solvent at a temperature of 20° C. to 30° C. for about 8 hours, then adjusting the reaction mixture to pH 2-3 with hydrochloric acid, and collecting the precipitated 1,5-dicyano-2,4-dioxo-3-azaspiro[5,5]-undecane by filtration.

As used herein, the term "lower alcohol solvent" refers to linear or branched $C_{1-6}$ alkyl alcohols, such as methanol, ethanol, propanol, isopropanol, butanol, t-butanol, hexanol, and mixtures thereof, preferably methanol and/or ethanol.

In addition, in the process for preparation of gabapentin hydrochloride according to the present invention, 1,5-dicyano-2,4-dioxo-3-azaspiro[5,5]-undecane used in step (i) is obtained by subjecting cyclohexanone and ethyl cyanoacetate to reaction with ammonia gas and/or aqueous ammonia in a lower alcohol solvent.

In particular, the process comprises: subjecting 1 mol of cyclohexanone and 2-2.5 mol of ethyl cyanoacetate to reaction with 3-5 mol of ammonia gas in a solvent of ethanol and/or methanol at a temperature of −5° C. to 5° C. for about 36 hours, allowing the reaction mixture to stand at room temperature for about 36 hours, then adjusting the reaction mixture to pH 2-3 with hydrochloric acid, and collecting the precipitated 1,5-dicyano-2,4-dioxo-3-azaspiro[5,5]-undecane by filtration. Or, alternatively, subjecting 1 mol of cyclohexanone and 2-2.5 mol of ethyl cyanoacetate to reaction with aqueous ammonia equivalent to 3-5 mol of ammonia gas at a temperature of −5° C. to 10° C. for about 24 hours, then heating the reaction mixture to a temperature of 20° C. to 25° C. and stirring for about 24 h, then further raising the temperature to 60° C., introducing water and adjusting the reaction mixture to pH 2-3 with sulfuric acid, then lowering the temperature to below 5° C. and collecting the precipitated 1,5-dicyano-2,4-dioxo-3-azaspiro[5,5]-undecane by filtration.

In the process for preparation of gabapentin hydrochloride according to the present invention, step (i) is carried out at a temperature of 65° C. to 85° C. by adding 1,5-dicyano-2,4-dioxo-3-azaspiro[5,5]-undecane into a strong acid over a period time of about 2.5 to 3.5 hours, wherein the weight ratio of 1,5-dicyano-2,4-dioxo-3-azaspiro[5,5]-undecane to the strong acid is 1:3 to 1:5.

Preferably, 1,5-dicyano-2,4-dioxo-3-azaspiro[5,5]-undecane is added into a strong acid in small portions over a period time of about 3 hours at a temperature of 78° C. to 82° C., wherein the weight ratio of 1,5-dicyano-2,4-dioxo-3-azaspiro [5,5]-undecane to the strong acid is 1:3.2; the reaction is completed when the mixture turns clear and the clear reaction solution is decanted into ice water, and the precipitated 1,5-diaminoformyl-2,4-dioxo-3-azaspiro[5,5]-undecane is collected by filtration, washed with water and dried. For this purpose, the strong acid may be, for example, concentrated hydrochloric acid, concentrated nitric acid, and/or concentrated sulfuric acid, preferably, 80-90% aqueous sulfuric acid solution, more preferably, 88% aqueous sulfuric acid solution.

Specifically, step (ii) of the preparation process for gabapentin hydrochloride according to the present invention comprises dissolving 1 mol of 1,5-diaminoformyl-2,4-dioxo-3- azaspiro[5,5]-undecane in 3-6 mol of 20-50% sodium hydroxide or potassium hydroxide solution and refluxing for about 2.5 to 3.5 hours, then allowing the alkaline solution to stand at 25° C. to 30° C. for about 24 hr, adding the alkaline solution into sodium hypochlorite solution with the temperature controlled within the range of −5° C. to 5° C. and mixing sufficiently, adding 35-45% sodium hydroxide or potassium hydroxide solution and mixing sufficiently, raising to a temperature of 45° C. to 70° C. and stirring for 1-2 hours, then adjusting the reaction mixture to pH 1-2 with hydrochloric acid, cooling the resulting acidic solution, collecting the precipitate by filtration and then drying to provide gabapentin hydrochloride.

In a preferred preparation processes of gabapentin hydrochloride, 1 mol of 1,5-diaminoformyl-2,4-dioxo-3-azaspiro[5,5]-undecane is dissolved in 3-6 mol of 20-50% sodium hydroxide or potassium hydroxide solution and the reaction mixture is refluxed for about 2.5 to 3.5 hours, the mixture is then adjusted to pH 1-2 with concentrated hydrochloric acid at a temperature of 70° C. to 80° C. and extracted with toluene at a temperature of 78° C. to 82° C., the toluene extract is then alkalized with 15-25% sodium hydroxide or potassium hydroxide solution and toluene is removed after the alkaline solution and toluene layers have been separated (which serves to remove impurities and purify the product), the alkaline solution is allowed to stand at a temperature of 25° C. to 30° C. for about 24 hr. The alkaline solution is then added into sodium hypochlorite solution with the temperature controlled at a temperature of −5° C. to 5° C. and mixed sufficiently, 35-45% sodium hydroxide or potassium hydroxide solution is added and mixed sufficiently, the reaction mixture is heated to a temperature of 45° C. to 70° C. and stirred for about 1-2 hours, then the reaction mixture is adjusted to pH 1-2 with hydrochloric acid and the resulting acidic solution is left to be cooled, the precipitate is collected by filtration, and dried to provide gabapentin hydrochloride.

In a more preferred preparation process, 1 mol of 1,5-diaminoformyl-2,4-dioxo-3-azaspiro[5,5]-undecane is dissolved in 5 mol of 40% potassium hydroxide solution and the reaction mixture is refluxed for 3 hours, then the reaction mixture is adjusted to pH 1-2 with concentrated hydrochloric acid at a temperature of 70° C. to 80° C., further refluxed for 1 hour, and extracted with toluene at 80° C., the toluene extract is then alkalized with 3 mol of 20% potassium hydroxide and toluene is removed after the alkaline solution and toluene layers have been separated, the alkaline solution is allowed to stand at a temperature of 25° C. to 30° C. for about 24 hours. With the temperature controlled at 0° C., the alkaline solution is then added into 1.2 mol of 8%-10% sodium hypochlorite solution and stirred for about 30 min, 3 mol of 40% potassium hydroxide is added and stirred for 30 min, the reaction mixture is heated to a temperature of 45° C. to 50° C. and stirred for about 1-2 hours, then the reaction mixture is adjusted to pH 1-2 with hydrochloric acid and is left to be cooled after impurities have been removed from the resulting acidic solution with toluene, the precipitate is collected by filtration, dried, and recrystallized from sec-butanol or isopropanol to provide gabapentin hydrochloride.

The present invention also comprises 1,5-diaminoformyl-2,4-dioxo-3-azaspiro[5,5]-undecane as an intermediate used in the preparation of gabapentin hydrochloride, and preparation process thereof, wherein the preparation process comprises: hydrolyzing 1,5-dicyano-2,4-dioxo-3-azaspiro[5,5]-undecane at a temperature of 65° C. to 85° C. in the presence of a strong acid.

Preferably, 1,5-dicyano-2,4-dioxo-3-azaspiro[5,5]-undecane is added into a strong acid in small portions at a temperature of 65° C. to 85° C. over a period time of 2.5 to 3.5 hours, wherein the weight ratio of 1,5-dicyano-2,4-dioxo-3-azaspiro[5,5]-undecane to the strong acid is 1:3 to 1:5.

More preferably, according to the above preparation process 1,5-dicyano-2,4-dioxo-3-azaspiro[5,5]-undecane is added into a strong acid in small portions at a temperature of 78° C. to 82° C. over a period time of about 3 hours, wherein the weight ratio of 1,5-dicyano-2,4-dioxo-3-azaspiro[5,5]-undecane to the strong acid is 1:3.2; the reaction is completed when the mixture turns clear and the clear solution is decanted into ice water, the precipitated 1,5-diaminoformyl-2,4-dioxo-3-azaspiro[5,5]-undecane is collected by filtration, washed with water, and then dried. For this purpose, the strong acid may be, for example, concentrated hydrochloric acid, concentrated nitric acid and/or concentrated sulfuric acid, preferably, 80-90% aqueous sulfuric acid solution, more preferably, 88% aqueous sulfuric acid solution.

1,5-dicyano-2,4-dioxo-3-azaspiro[5,5]-undecane is used as starting materials according to the present invention to form 1,5-diaminoformyl-2,4-dioxo-3-azaspiro[5,5]-undecane under an acid hydrolysis condition. 1,5-diaminoformyl-2,4-dioxo-3-azaspiro[5,5]-undecane is subjected to Hofmann rearrangement under an alkaline condition and is acidified with hydrochloric acid to yield gabapentin hydrochloride. The procedures are illustrated in the following scheme:

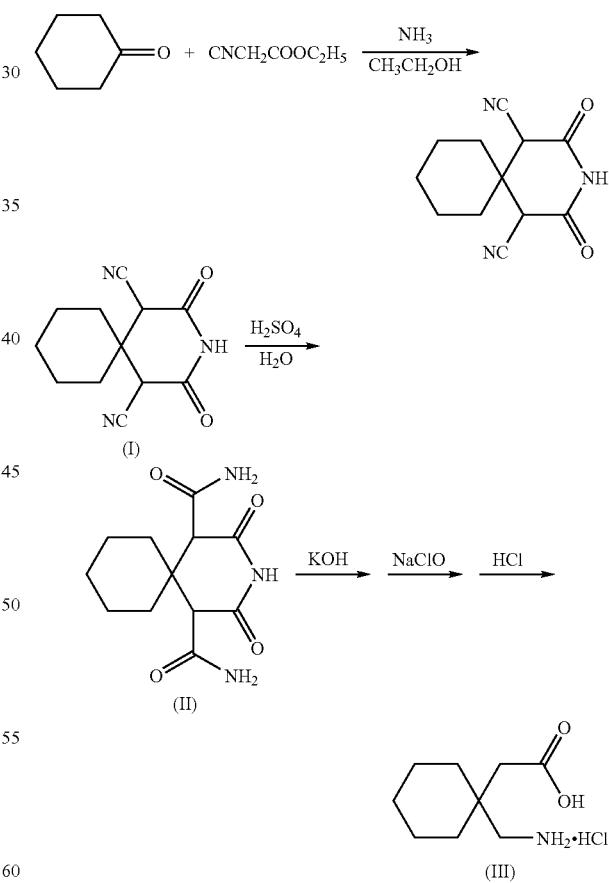

(I): 1, 5-dicyano-2, 4-dioxo-3-azaspiro[5, 5]-undecane;
(II): 1, 5-diaminoformyl-2, 4-dioxo-3-azaspiro[5, 5]-undecane;
(III): gabapentin hydrochloride The starting material of the process for preparation of gabapentin hydrochloride according to the present invention is readily available (for example, the starting materials are cyclohexanone, ethyl cyanoacetate, cyanoacetamide, etc.). The present process is simple, and can reduce the purification process of intermediates, reduce the production cost and obtain the product with higher purity.

EXAMPLES

The following commercially available reagents were used: cyclohexanone: industrial grade; ethyl cyanoacetate: industrial grade; cyanoacetamide: industrial grade; triethylamine: industrial grade; concentrated aqueous ammonia: $\geqq 25\%$ (calculated as 25% in the examples, but not limit to this concentration); methanol: industrial grade; sulfuric acid: industrial grade.

Example 1

1. Preparation of 1,5-dicyano-2,4-dioxo-3-azaspiro[5,5]-undecane 98 g (1 mol) of cyclohexanone, 113 g (1 mol) of ethyl cyanoacetate, 84 g (1 mol) of cyanoacetamide, and 100 ml of methanol were mixed in a reaction flask. 101 g (1 mol) of triethylamine was added dropwise under stirring, and the reaction mixture was stirred for 8 hours with the temperature controlled within the range of 25° C. to 30° C., and then was cooled and filtered. The filter cake was suspended in water, and the suspension was adjusted to pH 2-3 with concentrated hydrochloric acid while stirring. The suspension was filtered, washed with water, and dried to provide 1,5-dicyano-2,4-dioxo-3-azaspiro[5,5]-undecane. Yield: 88%, melting point: 202 to 210° C.

2. Preparation of 1,5-diaminoformyl-2,4-dioxo-3-azaspiro[5,5]-undecane (II)

231 g of 1,5-dicyano-2,4-dioxo-3-azaspiro[5,5]-undecane (I) was added into 739.2 g of 88% aqueous sulfuric acid solution (the weight ratio of (I) to aqueous sulfuric acid solution is 1:3.2) in small portions at about 80° C. (the temperature was controlled within the range of 78° C. to 82° C.) over a period time of about 3 hours. The reaction was completed in about 1 hour when the reaction mixture turned clear. The clear solution was decanted into ice water in a weight ratio of 1:10, and stirred for 30 min. The precipitate was collected by filtration, and the filter cake was washed with water, and dried to provide 1,5-diaminoformyl-2,4-dioxo-3-azaspiro[5,5]-undecane. Yield: 95%, melting point: >300° C.
IR spectrum: 3395, 3192, 3084 (—$NH_2$, —NH), 2932, 2863 (—$CH_2$), 1674, 1727 (C=O) $^1$H NMR ($\delta$, ppm, 400 MHz, DMSO-$d_6$): 1.332-1.887 (10H, m, —$CH_2$), 3.335 (2H, s, —CH), 7.227-7.864 (4H, s, —$NH_2$), 10.961 (1H, s, —NH) $^{13}$C NMR ($\delta$, ppm, 400 MHz, DMSO-$d_6$): 20.45-31.55 (5×$CH_2$), 38.37 ($CR_4$), 54.32-56.92 (2×CH), 166.30-170.68 (4×C=O) MS: m/z: 268 (M+H$^+$, 100%)

3. Preparation of Gabapentin Hydrochloride (III)

243 g (1 mol) of the above product 1,5-diaminoformyl-2,4-dioxo-3-azaspiro[5,5]-undecane was dissolved in 5 mol of 40% potassium hydroxide solution and refluxed for 3 hours. The pH value was adjusted to 1-2 with concentrated hydrochloric acid with the temperature controlled within the range of 70° C. to 75° C. The mixture was heated to reflux for 1 hour, and extracted with toluene at about 80° C. (precipitate may occur if the temperature is too low). The toluene layer was alkalized with 3 mol of 20% potassium hydroxide solution, after which toluene was removed and the alkaline solution was allowed to stand at 25° C. to 30° C. for 24 hr. The alkaline solution was then added dropwise into 1.2 mol of 10% sodium hypochlorite solution and the reaction mixture was stirred for 30 min. 3 mol of 40% potassium hydroxide solution was then added, and the reaction mixture was further stirred for 30 min. Then the reaction mixture was heated to 45° C. to 50° C., and stirred for another hour. The reaction mixture was adjusted to pH 1-2 with hydrochloric acid, left to be cooled after impurities had been extracted with toluene, and then filtered, dried, and recrystallized from sec-butanol to provide the subject compound. Yield: 50%, melting point: 116-125° C.

Example 2

1. Preparation of 1,5-dicyano-2,4-dioxo-3-azaspiro[5,5]-undecane 98 g (1 mol) of cyclohexanone, 226 g (2 mol) of ethyl cyanoacetate, and 392 g of 96% methanol were mixed in a reaction flask, to which 272 g of aqueous ammonia (equivalent to 4 mol of ammonia gas) was added under stirring. Specifically, to carry out the addition of aqueous ammonia, the temperature was lowered to within the range of −5° C. to 0° C., ¾ of the prescribed amount of aqueous ammonia was added dropwise, the reaction mixture was then stirred for a first 12 hours with the temperature maintained at −5° C. to 0° C., and a second 12 hours with the temperature maintained at 5 to 10° C., and then the rest ¼ of aqueous ammonia was added. The reaction mixture was heated to and maintained at 20° C. to 25° C. for 24 hours under stirring. The mixture was then heated to 60° C., to which water was added in an amount equivalent to methanol, that is, 980 g water was added. The pH value was adjusted to 2-3 with dropwise addition of sulfuric acid, after which the temperature was lowered to below 5° C. and the mixture was centrifugally filtered. The filter cake was washed with water to pH 6-7, filtered, and dried to provide 1,5-dicyano-2,4-dioxo-3-azaspiro[5,5]-undecane. Yield: 85%, melting point: 202-210° C.

2. Preparation of 1,5-diaminoformyl-2,4-dioxo-3-azaspiro[5,5]-undecane (II)

231 g of 1,5-dicyano-2,4-dioxo-3-azaspiro[5,5]-undecane was added into 739.2 g of 88% sulfuric acid solution in small portions at 78° C. to 82° C. over a period time of 3 hours, wherein the weight ratio of 1,5-dicyano-2,4-dioxo-3-azaspiro [5,5]-undecane to sulfuric acid solution is 1:3.2. The reaction mixture was mixed sufficiently for 1 hour, and the reaction was completed when the reaction mixture turned clear. The resulting clear solution was decanted into ice water in a weight ratio of 1:10, and was then stirred for 30 min. The precipitate was collected by filtration. The filer cake was washed with water, and then dried to provide 1,5-diaminoformyl-2,4-dioxo-3-azaspiro[5,5]-undecane. Yield: 95%, melting point: >300° C.

3. Preparation of Gabapentin Hydrochloride (III)

243 g (1 mol) of the above product 1,5-diaminoformyl-2,4-dioxo-3-azaspiro[5,5]-undecane was dissolved in 5 mol of 40% potassium hydroxide solution and was refluxed for 3 hours. The pH value was adjusted to 1-2 with concentrated hydrochloric acid with the temperature controlled within the range of 75° C. to 80° C. The mixture was heated to reflux for 1 hour, then extracted with toluene at about 80° C. (precipitate may occur if the temperature is too low). The toluene layer was alkalized with 3 mol of 20% potassium hydroxide solution. Then toluene was removed and the alkaline solution was allowed to stand at 25° C. to 30° C. for 24 hr. With the temperature controlled at 0° C., the alkaline solution was added dropwise into 1.2 mol of 8% sodium hypochlorite solution and the reaction mixture was stirred for 30 min. 3 mol of 40% potassium hydroxide solution was then added, and the reaction mixture was further stirred for 30 min. Then the reaction mixture was heated to 45° C. to 50° C. and stirred for 1-2 h. The reaction mixture was adjusted to pH 1-2 with hydrochloric acid, left to be cooled after impurities had been extracted with toluene, and then filtered, dried, and recrystallized from sec-butanol to provide the subject compound. Yield: 45%, melting point: 116 to 125° C.

Example 3

1. Preparation of 1,5-dicyano-2,4-dioxo-3-azaspiro[5,5]-undecane 98 g (1 mol) of cyclohexanone and 226 g (2 mol) of ethyl cyanoacetate were reacted with 204 g aqueous ammonia (equivalent to 3 mol of ammonia gas) in a solvent of methanol. After reacted at −5° C. to 0° C. for 24 hours, the reaction mixture was heated to 20 to 25° C. and stirred for 24 hours, and then heated to 60° C. Water is added in an amount equal to methanol, and the mixture was adjusted to pH 2-3 with sulfuric acid. The mixture was then cooled to below 5° C. and the precipitated 1,5-dicyano-2,4-dioxo-3-azaspiro[5,5]-undecane was collected by filtration.

2. Preparation of 1,5-diaminoformyl-2,4-dioxo-3-azaspiro[5,5]-undecane (II)

231 g of 1,5-dicyano-2,4-dioxo-3-azaspiro[5,5]-undecane was added in small portions into 762 g of 80% sulfuric acid solution (consisting of 80% of sulfuric acid and 20% of water) at a temperature of 65° C. to 70° C. over a period time of 2.5 hours, wherein the weight ratio of 1,5-dicyano-2,4-dioxo-3-azaspiro[5,5]-undecane to the sulfuric acid solution is 1:3. The reaction was completed when the mixture turned clear. The clear reaction mixture was decanted into ice water in a weight ratio of 1:10, and stirred for 30 min. The precipitated 1,5-diaminoformyl-2,4-dioxo-3-azaspiro[5,5]-undecane was collected by filtration, washed with water, and then dried to provide 1,5-diaminoformyl-2,4-dioxo-3-azaspiro[5,5]-undecane. Yield: 90%, melting point: >300° C.

3. Preparation of Gabapentin Hydrochloride (III)

243 g (1 mol) of 1,5-diaminoformyl-2,4-dioxo-3-azaspiro[5,5]-undecane was dissolved in 3 mol of 20% sodium hydroxide solution and was refluxed for 2.5 hours. The pH value was adjusted to 1-2 with concentrated hydrochloric acid at 70° C. to 75° C. The mixture was refluxed for 1 hour, and extracted with toluene at 78° C. to 82° C. The toluene extract was alkalized with 3 mol of 25% sodium hydroxide solution. Toluene was removed after the alkaline solution and toluene layers had been separated, and the alkaline solution was allowed to stand at 25° C. to 30° C. for 24 hr. The alkaline solution was added into 1.2 mol of 8% sodium hypochlorite solution with the temperature controlled at −5° C. to 0° C., and the reaction mixture was further stirred for 30 min. 3 mol of 45% sodium hydroxide solution was added and the mixture was stirred for 30 min. After heated to 45° C. to 50° C. and stirred for 1-2 hours, the reaction mixture was adjusted to pH 1-2 with hydrochloric acid. The resulting acidic solution was left to be cooled, and the precipitate was collected by filtration and dried to provide gabapentin hydrochloride.

Example 4

1. Preparation of 1,5-dicyano-2,4-dioxo-3-azaspiro[5,5]-undecane 98 g (1 mol) of cyclohexanone and 282.5 g (2.5 mol) of ethyl cyanoacetate were reacted with 340 g aqueous ammonia (equivalent to 5 mol of ammonia gas) in a solvent of ethanol. After reacted at 5 to 10° C. for 24 hours, the mixture was heated to 25° C. and stirred for another 24 hours. The temperature was raised to 60° C. and water was added in an amount equivalent to the ethanol. The pH value was adjusted to 2 to 3 with sulfuric acid. The temperature was lowered to below 5° C. and the precipitated 1,5-dicyano-2,4-dioxo-3-azaspiro[5,5]-undecane was collected by filtration.

2. Preparation of 1,5-diaminoformyl-2,4-dioxo-3-azaspiro[5,5]-undecane (II)

231 g of 1,5-dicyano-2,4-dioxo-3-azaspiro[5,5]-undecane was added into 1129 g of 90% sulfuric acid solution (consisting of 90% sulfuric acid and 10% water) in small portions at 80° C. to 85° C. over a period time of 3.5 hours, wherein the weight ratio of 1,5-dicyano-2,4-dioxo-3-azaspiro[5,5]-undecane to sulfuric acid solution is 1:5. The reaction was completed when the mixture turned clear. The resulting clear solution was decanted into ice water in a weight ratio of 1:10 and was then stirred for 30 min. The precipitated 1,5-diaminoformyl-2,4-dioxo-3-azaspiro[5,5]-undecane was collected by filtration, washed with water, and dried to provide 1,5-diaminoformyl-2,4-dioxo-3-azaspiro[5,5]-undecane. Yield: 92%, melting point: >300° C.

3. Preparation of Gabapentin Hydrochloride (III)

243 g (1 mol) of the 1,5-diaminoformyl-2,4-dioxo-3-azaspiro[5,5]-undecane was dissolved in 6 mol of 50% potassium hydroxide solution and was refluxed for 3.5 hours. The pH value was then adjusted to 1-2 with concentrated hydrochloric acid at 75° C. to 80° C. The mixture was extracted with toluene at 80° C., and the toluene extract was alkalized with 3 mol of 15% potassium hydroxide solution. Then toluene was removed after alkaline solution and toluene layers had been separated and the alkaline solution was allowed to stand at 25° C. to 30° C. for 24 hr. The alkaline solution was added into 1.2 mol of 10% sodium hypochlorite solution with the temperature controlled at 0° C. to 5° C., and the reaction mixture was stirred for 30 min. 3 mol of 35% potassium hydroxide solution was then added, and the reaction mixture was stirred for 30 min. The reaction mixture was raised to 65° C. to 70° C., and was further stirred for 1-2 hr. The pH value was adjusted to 1-2 with hydrochloric acid and the resulting acidic solution was left to be cooled. The precipitate was collected by filtration and dried to provide gabapentin hydrochloride.

What is claimed is:

1. Process for preparation of gabapentin hydrochloride which comprises:
(i) converting 1,5-dicyano-2,4-dioxo-3-azaspiro [5,5]-undecane into 1,5-diaminoformyl-2,4-dioxo-3-azaspiro[5,5]-undecane at a temperature of about 78° C. to 82° C. in the presence of a strong acid; and
(ii) subjecting 1,5-diaminoformyl-2,4-dioxo-3-azaspiro[5,5]-undecane obtained in step (i) to Hofmann rearrangement under an alkaline condition and acidifying with hydrochloric acid to provide gabapentin hydrochloride, wherein in step (ii), 1 mol of 1,5-diaminoformyl-2,4-dioxo-3-azaspiro,[5]-undecane is dissolved in 3-6 mol of 20-50% sodium hydroxide or potassium hydroxide solution, the reaction mixture is refluxed for about 2.5 to 3.5 hours and then allowed to stand at a temperature of 25° C. to 30° C. for about 24-hours, the alkaline solution is added into sodium hypochlorite solution with the temperature controlled at about −5° C. to 5° C., 35-45% sodium hydroxide or potassium hydroxide solution is then added, and the reaction mixture is heated to a temperature of about 45° C. to 70° C., stirred for about 1-2 hours, and adjusted to pH 1-2 with hydrochloric acid to provide gabapentin hydrochloride.

2. The process for preparation of gabapentin hydrochloride according to claim 1, wherein 1,5-dicyano-2,4-dioxo-3-azaspiro[5,5]-undecane used in step (i) is prepared by subjecting cyclohexanone, ethyl cyanoacetate, cyanoacetamide, and triethylamine to reaction in a lower alcohol solvent.

3. The process for preparation of gabapentin hydrochloride according to claim 2, wherein cyclohexanone, ethyl cyanoacetate, cyanoacetamide, and triethylamine are in a molar ratio of 1:1:1:1, the lower alcohol is methanol, and the reaction is carried out at a temperature of about 20° C. to 30° C.

4. The process for preparation of gabapentin hydrochloride according to claim 1, wherein 1,5-dicyano-2,4-dioxo-3-azaspiro[5,5]-undecane used in step (i) is prepared by subjecting cyclohexanone and ethyl cyanoacetate to reaction with ammonia gas and/or aqueous ammonia in a lower alcohol solvent.

5. The process for preparation of gabapentin hydrochloride according to claim 4, wherein 1,5-dicyano-2,4-dioxo-3-azaspiro[5,5]-undecane used in step (i) is prepared by subjecting 1 mol of cyclohexanone and 2-2.5 mol of ethyl cyanoacetate to reaction with 3-5 mol of ammonia gas in a solvent of ethanol and/or methanol at a temperature of about −5° C. to 5° C.

6. The process for preparation of gabapentin hydrochloride according to claim 4, wherein 1,5-dicyano-2,4-dioxo-3-azaspiro[5,5]-undecane used in step (i) is prepared by subjecting 1 mol of cyclohexanone and 2-2.5 mol of ethyl cyanoacetate to reaction with aqueous ammonia equivalent to 3-5 mol of ammonia gas in a solvent of ethanol and/or methanol at a temperature of about −5° C. to 10° C.

7. The process for preparation of gabapentin hydrochloride according to claim 1, wherein the strong acid is 80-90% aqueous sulfuric acid solution, and 1,5-dicyano-2,4-dioxo-3-azaspiro[5,5]-undecane and the sulfuric acid solution are in a weight ratio of about 1:3 to 1:5.

8. The process for preparation of gabapentin hydrochloride according to claim 7, wherein the strong acid is 88% aqueous sulfuric acid solution, and the weight ratio of 1,5-dicyano-2,4-dioxo-3-azaspiro[5,5]-undecane to the sulfuric acid solution is about 1:3.2.

9. The process for preparation of gabapentin hydrochloride according to claim 1, wherein 1 mol of 1,5-diaminoformyl-2,4-dioxo-3-azaspiro[5,5]-undecane is dissolved in 3-6 mol of 20-50% sodium hydroxide or potassium hydroxide solution and the reaction mixture is refluxed for about 2.5 to 3.5 hours, adjusted to pH 1-2 with concentrated hydrochloric acid at a temperature of 70° C. to 80° C., and then extracted with toluene at a temperature of 78° C. to 82° C., the toluene extract is alkalized with 15-25% sodium hydroxide or potassium hydroxide solution and toluene is removed after alkaline solution and toluene layers have been separated, the alkaline solution is allowed to stand at a temperature of 25° C. to 30° C. for about 24 hours, then the alkaline solution is added into sodium hypochlorite solution with the temperature controlled at −5° C. to 5° C. and mixed sufficiently, 35-45% sodium hydroxide or potassium hydroxide solution is added and mixed sufficiently, and the reaction mixture is heated to a temperature of 45° C. to 70° C., stirred for about 1-2 hours, and then adjusted to pH 1-2 with hydrochloric acid to provide gabapentin hydrochloride.

10. The process for preparation of gabapentin hydrochloride according to claim 9, wherein 1 mol of 1,5-diaminofonnyl-2,4-dioxo-3-azaspiro[5,5]-undecane is dissolved in 5 mol of 40% potassium hydroxide solution and the reaction mixture is refluxed for about 3 hours, adjusted to pH 1-2 with concentrated hydrochloric acid at 80° C., further refluxed for about 1 hour, and then extracted with toluene at 80° C., the toluene extract is alkalized with 3 mol of 20% potassium hydroxide solution and toluene is removed after alkaline solution and toluene layers have been separated, the alkaline solution is allowed to stand at a temperature of 25° C. to 30° C. for about 24 hours, then the alkaline solution is added into 1.2 mol of 8% −10% sodium hypo chlorite solution with the temperature controlled at 0° C. and stirred for 30 min, 3 mol of 40% potassium hydroxide solution is added and the mixture is further stirred for 30 min, the reaction mixture is heated to 45° C. to 50° C. and stirred for about 1-2 hours, then the reaction mixture is adjusted to pH 1-2 with hydrochloric acid and impurities are removed from the resulting acidic solution with toluene, and the precipitate is recrystalized from sec-butanol or isopropanol to provide gabapentin hydrochloride.

11. The process for preparation of gabapentin hydrochloride according to claim 2 wherein the strong acid is 80-90% aqueous sulfuric acid solution, and 1,5-dicyano-2,4-dioxo-3-azaspiro[5,5]-undecane and the sulfuric acid solution are in a weight ratio of about 1:3 to 1:5.

12. The process for preparation of gabapentin hydrochloride according to claim 3 wherein the strong acid is 80-90% aqueous sulfuric acid solution, and 1,5-dicyano-2,4-dioxo-3-azaspiro[5,5]-undecane and the sulfuric acid solution are in a weight ratio of about 1:3 to 1:5.

\* \* \* \* \*